United States Patent [19]

Landay

[11] Patent Number: 5,108,904
[45] Date of Patent: Apr. 28, 1992

[54] CD44 AS A MARKER FOR HIV INFECTION

[76] Inventor: Alan Landay, 1005 N. East Ave., Oak Park, Ill.

[21] Appl. No.: 499,144

[22] Filed: Mar. 26, 1990

[51] Int. Cl.$^5$ .......................................... G01N 33/533
[52] U.S. Cl. ...................................... 435/7.24; 435/5; 435/7.1; 435/7.2
[58] Field of Search ...................... 435/5, 7.1, 7.2, 7.24

[56] References Cited

U.S. PATENT DOCUMENTS

| | | | |
|---|---|---|---|
| 3,826,364 | 7/1974 | Bonner | 209/3 |
| 4,284,412 | 8/1981 | Hansen | 23/230 |
| 4,452,773 | 5/1984 | Molday | 264/1 |
| 4,520,110 | 5/1985 | Stryer | 436/501 |
| 4,607,007 | 8/1986 | Lanier et al. | 435/7.24 |
| 4,661,913 | 4/1987 | Wu | 364/500 |
| 4,727,020 | 2/1988 | Recktenwald | 435/6 |
| 5,002,873 | 3/1991 | St. John et al. | 435/69.1 |

OTHER PUBLICATIONS

Redfield et al., Sci. Amer., 259 70 (1988).
Weber et al., Sci. Amer., 259:80 (1988).
Leukocyte Typing IV, pp. 619-27 (1989).
Kohler et al., Nature 276 269 (1978).
Herzenberg et al., Sci. Amer. 234 108 (1976).

*Primary Examiner*—Christine Nucker
*Assistant Examiner*—Jeffrey Stucker
*Attorney, Agent, or Firm*—Robert M. Hallenbeck

[57] ABSTRACT

A method for discriminating between patients who are seropositive but asymptomatic for HIV infection and AIDS patients is disclosed wherein the fluorescence intensity from CD44$^+$ T cells is measured. Intensity increases as AIDS progresses.

11 Claims, 2 Drawing Sheets

CD44 AS A MARKER FOR HIV INFECTION

FIELD OF THE INVENTION

This invention relates to a novel assay for the detection of immunological changes associated with viral infection and more particularly relates to an assay involving the use of monoclonal antibodies against CD44 for detecting immunological changes associated with the transition from asymptomatic seropositive human immunodeficiency virus ("HIV") infection to AIDS.

BACKGROUND OF THE INVENTION

AIDS is a clinically defined medical illness which can result from an infection with HIV. The definition of AIDS has been published and continually revised by the Centers for Disease Control (Atlanta). It is generally accepted that progression of the infection gradually renders the individual immunodeficient, and as a result, HIV leads to death from fatal opportunistic infections such as *Pneumocystis carinii* pneumonia. The mechanism by which HIV infection results in AIDS is believed to be mediated through the binding of HIV to a subset of T cells which are identified by the CD4 and CD3 surface antigens. By infecting and subsequently destroying the CD4 subset of lymphocytes, the individual infected with HIV loses the ability to respond to certain infectious agents.

HIV infections progress through a number of clinical stages which may be distinguished in both clinical and laboratory findings. One presently accepted classification system for defining and staging the progress of HIV infection from initial exposure through the diagnosis of AIDS is described in the Walter Reed Classification System. This system is set out in Table I.

TABLE I

| Stage | Ab/Virus | Chronic Lymphad-enopathy | CD4 Cells (cells/mm$^2$) | Delayed Hyper-sensitivity | Thrush | Oppor-tunistic Infec-tions |
|---|---|---|---|---|---|---|
| WR0 | − | − | >400 | Normal | − | − |
| WR1 | + | − | >400 | Normal | − | − |
| WR2 | + | + | >400 | Normal | − | − |
| WR3 | + | + | <400 | Normal | − | − |
| WR4 | + | + | <400 | Partial | − | − |
| WR5 | + | + | <400 | Complete and/or | + | − |
| WR6 | + | + | <400 | Complete | + | + |

As may be seen from Table I, a number of separate criteria go into evaluating and defining each of the several stages. For example, the presence or absence of antibodies (Abs) to HIV or the presence or absence of detectable virus itself are used as an indication of initial exposure to HIV (WR1). These infected patients exhibit few, if any, signs of AIDS and may be considered asymptomatic but seropositive. Subsequently, the number of CD4 cells falls, the further the disease has progressed (WR3). These patients are still asymptomatic. At stage WR4, however, the seropositive patient is defined as no longer being asymptomatic but may be defined as having AIDS. For a further description of the Walter Reed Classification System and the clinical aspects of AIDS, see Redfield et al., Sci. Amer., 259:70 (1988).

While the Walter Reed Classification System provides a means for monitoring and staging the progress of an individual's disease, the system is based, at least initially, on the ability to quantify the number of CD4 cells present in a sample and/or detect the presence of anti HIV antibodies or virus in a sample. Unfortunately, currently available techniques for the detection of antibodies or virus have certain limitations. It is known, for example, to use recombinant or synthetic gp120 (an HIV viral envelope antigen) as a capture antigen in a serum based assay. This method, however, assumes that the progression of the disease in the individual is to such a state that not only are antibodies being made against HIV but that the antibodies made by the individual will react with synthetic gp120 and in sufficient quantity so as to be detectable. Indeed, early antibody responses may be masked by the presence of free virus in peripheral blood.

Similarly, using the reverse approach, antibodies against gp120 and other viral antigens (e.g., p24) may be made and used to detect the presence of virus or viral protein in a sample of blood from an individual. Although this is an antigen capture based method, its use assumes that the detecting antibodies will react with all forms of HIV which may be present in any particular infection and assumes that the viral particles are present in the serum sample; a limitation, however, is that virus particles are only transiently present in serum.

A further method for evaluating the serological response of an infected individual involves the use of the Western blotting technique wherein a serum sample derived from an individual is incubated with a piece of filter paper to which an electrophoretically separated preparation of HIV protein antigens have been fixed. If antibody is present in the serum sample then a precipitation product is generated and it may be assumed that antibodies are present to specific viral proteins. Again, this assay is based on the infected individuals serological response to the HIV virus.

Apart from these presently practiced techniques, other methods have been tried to identify HIV infection. Changes in the number of cellular immune effectors such as the number of CD4+ T cells or the ratio of CD4+ to CD8+ cells also have been used to identify and stage HIV infection. As noted above, the number of CD4+ T cells provides one basis for the Walter Reed Classification System. The ratio of CD4+ to CD8+ cells also may be indicative of the progression of the HIV infection. Finally, still other studies have reported that with HIV infection the number of HLA-DR+T cells or the number of CD8+/CD38+ cells increases.

Because of the variable time course of appearance of certain of these markers and because of the potential unreliability of a number of these presently practiced techniques and often, a number of these techniques are used in concert in order to determine whether an individual has been exposed to HIV and has either made an antibody response or has the virus in the blood. This approach is both costly and time consuming.

In all cases, it is important to determine the transition from asymptomatic seropositive to AIDS. Knowing when this transition occurs will allow the physician to prescribe a more rigorous course of treatment. Accordingly, a rapid/early and reliable means for detecting the transition from a condition of asymptomatic seropositive to AIDS in the course of HIV infection is needed.

SUMMARY OF THE INVENTION

The present invention comprises a novel assay for the detection of immunological changes associated with a viral infection, and in particular with an HIV infection, which detects a change from an asymptomatic seropositive condition to AIDS.

The assay comprises a method for rapidly determining the number of CD44+ cells present in a sample. Surprisingly, it has been found that the density of CD44 antigen expression on CD44+ cells and the number of such cells significantly increases with the change from an asymptomatic seropositive condition to AIDS in the course of HIV infection. In particular, an increase in the density of CD44 antigen on CD8+ T cells and number of such cells correlates highly with this transition. Accordingly, by labelling CD44+ leukocytes in a sample, particularly lymphocytes and more particularly CD8+ T cells, the expression of CD44 can be determined and compared against values for normal and for asymptomatic seropositive individuals. In addition, the density of CD18 and/or CD54 expression on CD8+ T cells can be determined in the same sample and the combination of parameters may be used to identify the transition of HIV infected individuals from an asymptomatic stage to AIDS.

DETAILED DESCRIPTION OF THE INVENTION

Figure 1A:
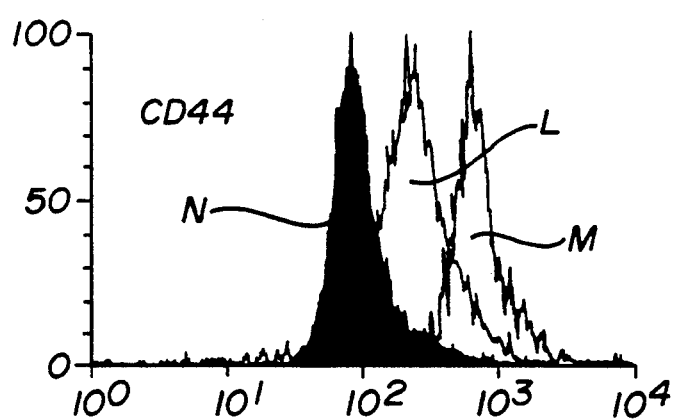
FIG. 1 comprises histograms of fluorescence intensity for neutrophils (N), lymphocytes (L) and monocytes (M) from normal (seronegative) individuals wherein the cells were isolated from peripheral blood and were treated with A) CD44, B) CD54 and C) CD18.

The present invention comprises a method of determining whether an individual has been exposed to a virus, particularly HIV, which results in immunological changes in the individual. In this method, a blood or other cell containing sample is collected from an individual. The sample then is treated to identify the cells expressing the CD44 antigen. The treated cells then are analyzed by means capable of discriminating between cells expressing CD44 and cells lacking CD44 and capable of discriminating between the level of CD44 expression on the CD44+ cells. The amount of CD44 expressed then is compared to values of a normal individual. Preferentially, the expression of CD44 is determined on T cells. Most preferentially, expression of CD44 on CD8+ T cells is determined.

In this method, preferentially, the sample comprises peripheral whole blood. Peripheral whole blood may be further treated to remove erythrocytes by means of lysis (leaving only leukocytes) or may be further treated by means of density gradient separation to prepare mononuclear cells (i.e., lymphocytes and monocytes). Alternatively, leukocytes or T cells may be isolated from peripheral whole blood by means of magnetically activated cell separation. In this procedure, magnetic microspheres of the type described in U.S. Pat. No. 4,452,773 are conjugated to a pan leukocyte antibody (anti-CD45) such as Anti-HLe-1 (BDIS), or a pan-T cell antibody (anti CD5) such as Anti-Leu 1 (BDIS). The antibody magnetic bead conjugate then may be mixed with the fluid sample and poured through and over the column containing a magnet. Cells bound to antibody will be retained in the column while cells not bound will be passed through. By removing the column from the permanent magnet, leukocytes or T cells can be collected.

Whether prepared by erythrocyte lysis or by density dependent centrifugation, mononuclear cells and T cells therein may be identified by tagging agents such as antibodies, preferentially monoclonal antibodies. Monoclonal antibodies against CD5 may be prepared by the methods of Kohler and Milstein infra or may be obtained commercially as, for example, Anti-Leu 1. It should be noted that this step could be omitted if T cells were initially isolated from peripheral blood by means such as magnetically activated cell sorting.

T cells expressing CD44 may be identified in the sample by means of treating the sample with antibodies, preferentially monoclonal antibodies, directed against the CD44 antigen. CD44+ cells are by convention cells which express the CD44 antigen. The CD44 antigen is a transmembraneous molecule with extensive O-linked glycosylation with an extracellular domain having six N-linked glycosylation sites. It has a molecular weight of between 80–95 kD. It is found principally on leukocytes and erythrocytes. (The "CD" designation is the internationally accepted standard by which leukocyte antigens and antibodies thereto are classified.)

Monoclonal antibodies against CD44 have been prepared by a number of persons. For a description of CD44 and antibodies made by others thereto, see Leukocyte Typing IV, pp. 619–627, Knapp et al., eds. (1989). Monoclonal antibodies may be made by conventional hybridoma technologies, such as those described by Kohler and Milstein, Nature, 276:269 (1978), using gamma/delta T cell receptor positive thymus T cells as the immunogen, for example. Clone L178 was made by using these cells to immunize Balb/C mice. Spleen cells from the immunized were fused with cells from the mouse myeloma cell line SP2/0 in accordance with known procedures. The resulting hybridomas were subcloned and L178 was isolated.

In order to identify T cells bearing CD44 and/or CD8 antigens, the antibodies used to treat the cells are conjugated to fluorescent labels which have different emission spectra and, preferentially, are excitable at the same wavelength of excitation. Two labels having these properties are the fluorochromes fluorescein isothiocyanate (FITC) and phycoerythrin (PE). Other pairs of fluorochromes may be selected from the group consisting of FITC, phycoerythrin, Texas red (Molecular Probes), C phycocyanine, allophycocyanine, and peridin-chlorophyll complex.

Cells treated with the fluorochrome conjugated monoclonal antibodies then are examined using means to excite the fluorochromes present and to detect the fluorochrome emissions. Preferentially, such means comprise a flow cytometer wherein treated cells are passed substantially one at a time through a sensing region where light of excitation wavelength illuminates each cell and further wherein scattered light and fluorescence emitted by each cell is collected, recorded and stored in associated hardware and software. The emission and light scatter data so recorded for each cell then may be analyzed by means of differential fluorescence intensities for each of the cell types treated. In the most preferred embodiment, the relative fluorescence expression of fluorescently labelled CD44+ is measured on fluorescently labelled CD8+ cells as determined by flow cytometry. Alternative means include fluorescence microscopy and image analysis.

Flow cytometry and flow cytometers generally are described in U.S. Pat. Nos. 4,661,913, 4,284,412, and 3,826,364, and in an article by Herzenberg et al., Sci. Amer., 234:108 (1976). In principle, they operate to identify different populations of leukocytes in a heterogeneous sample by detecting multiple independent parameters on the individual cells that pass through one or more sensing regions substantially one at a time. Each sensing region essentially comprises an area illuminated by the light of a single wavelength and from which light is collected by an array of photomultiplier tubes. Each photomultiplier tube measures a separate parameter. Typically, these parameters include forward light scatter (or FLS, which is a measure of relative particle size), orthogonal light scatter (or OLS, which is a measure of relative granularity or special complexity) and fluorescence emission(s) (generally referred to as FL1, etc.).

Fluorescence may be measured from cells that incorporate a nucleic acid stain and/or may be measured from cells bearing surface markers which are labelled with monoclonal antibodies which have been conjugated directly or indirectly with fluorochromes. One method for conjugation of PE is described in U.S. Pat. No. 4,520,110. In the indirect method, second step antibodies, for example, fluorescently labelled goat anti-mouse antibodies are used as a second step reagent to detect the presence of the mouse derived primary monoclonal antibodies which react with the antigen of interest. Fluorochromes and stains may be referred to as fluorescent labels.

It is important that if more than one fluorescent label is used that each label have a different wavelength of emission in order that fluorescence emission form each will minimally overlap. Generally, FITC and PE meet this criteria and are used. It is preferable that the labels also be excitable at the same wavelength. This allows the cells to be in the sample to be passed through one sensing region and exposed to light of a single wavelength (e.g., from an argon laser at 488nm). In other embodiments, the flow cytometer may have more than one sensing region. In one such embodiment, a dual laser source may be used where the labels selected are not excitable at the same wavelength.

Separate detector channels within the flow cytometer are able to sense light emitted or scattered for each of the various cell parameter measurements. In a typical configuration four or more parameters are measured (e.g., FLS, OLS, FL1 & FL2). Signals from these detectors for each cell passing through the sensing region are collected and may be stored for later data analysis by appropriately equipped recording means (e.g., a personal computer) and software (e.g., Consort 30 software or FACScan Research software, BDIS). By combining and comparing these parameters, the various leukocyte components may be identified and distinguished. U.S. Pat. No. 4,727,020 provides one example of how a flow cytometer may be used in this method to obtain leukocyte differentials from blood.

In order to identify CD44+ T cells that also are CD8+, fluorescently labelled monoclonal antibodies against both CD44 and CD8 may be used. (CD8 is a lineage specific surface antigen expressed on the cytotoxic/suppressor subset of T cells.) By using monoclonals conjugated with fluorochromes that fluoresce at different wavelengths, cells that express CD44 alone, CD8 alone and both CD8 and CD44 antigens can be identified and counted. In addition, the intensity of fluorescence can be determined. Fluorescence intensity may be correlated with the amount of fluorescently labelled antibodies that bind to the cell, thus, giving a measure of the antigen density per cell.

In addition to measuring the relative fluorescence expression of CD44+ T cells, the relative fluorescence expression of one or more of the following antigens also may be determined as a measure of HIV infection transition. In this embodiment, the expression of CD18 and/or CD54 positive T cells can be determined. CD18 is an antigen of approximately 180 kD which is present on leukocytes and is the beta chain of the LFA-1 molecule. CD54 is an antigen on endothelial cells having a molecular weight of 90 kD. CD54 also is known as ICAM-1. Both antigens are further described in Leukocyte Typing IV, supra.

In order to determine the relative fluorescence intensity and number of CD44 on CD8+ T cells, normal blood was collected in an evacuated tube containing ethylenediamenetetracetate ($K_3$). Aliquots of blood then were treated at room temperature for 15-30 minutes with Anti-Leu 2a FITC or PE (anti-CD8, BDIS), anti-CD44 PE (clone L178, BDIS), anti-CD18 FITC (clone L130, BDIS) and/or anti-CD54 PE (clone LB-2, BDIS). The treated cells then were lysed. The cells were washed in phosphate buffered saline/azide containing 3% fetal calf serum and resuspended in the same mixture. (To inactivate HIV, the cells could be fixed in a solution of 1% paraformaldehyde overnight.) Treated cells were analyzed on a FACScan brand flow cytometer (BDIS) equipped with a 15 mW argon laser. List mode data was stored and analyzed using Consort 30 software. Lymphocytes were identified by gating on FLS and OLS.

Figure 1B:
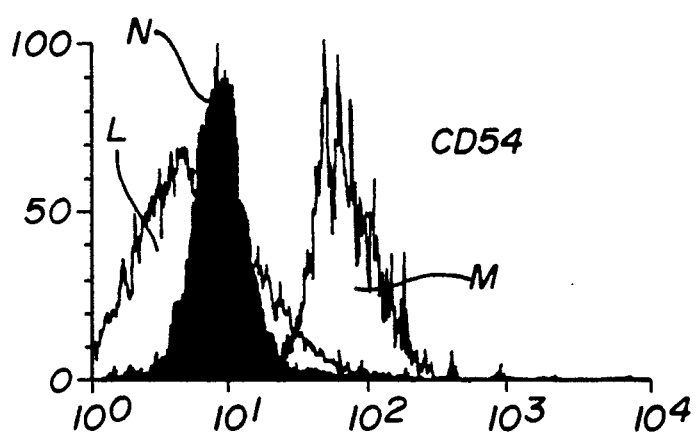
Figure 1C:
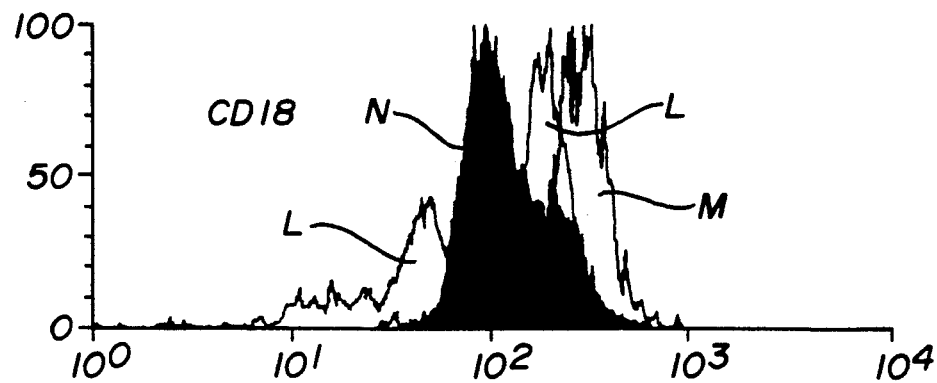

Turning to FIG. 1, peripheral blood from normal (seronegative) individuals was obtained as above. Monocytes, lymphocytes and neutrophils were identified by light scatter. The cells then were treated with A) anti-CD44, B) anti-CD18 and C) anti-CD54 antibodies as above. Gates were set for each population of cells and fluorescence histograms for A) CD44+, B) CD18+ and C) CD54+ cells were determined.

In the second experiment, peripheral blood was collected from asymptomatic seropositive patients and AIDS patients. The blood was fractionated by density dependent centrifugation to collect mononuclear cells which were treated with monoclonal antibodies as above.

Figure 2A:
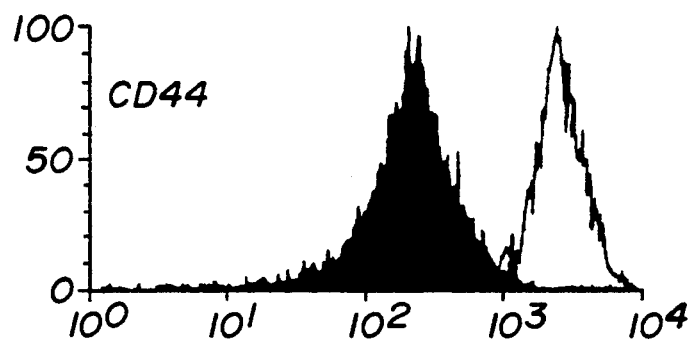
FIG. 2 comprises histograms of fluorescence intensity for mononuclear cells treated with A) CD44, B) CD54 and C) CD18 wherein the cells were isolated from the blood of asymptomatic/seropositive and AIDS patients (dark curve).
Figure 2B:
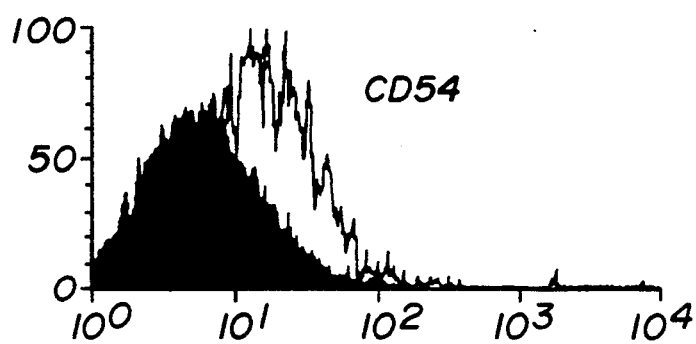
Figure 2C:
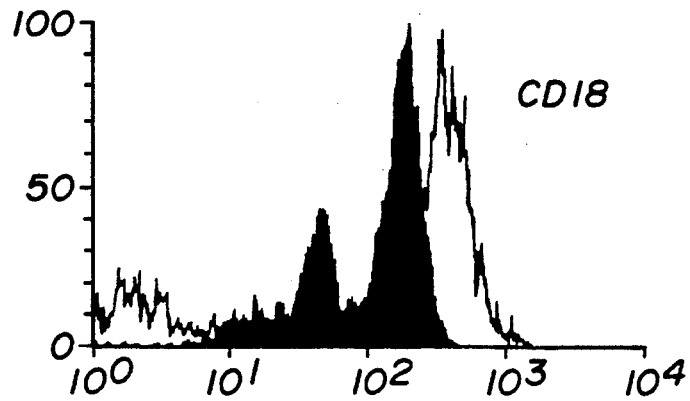

Turning to FIG. 2, it can be seen that individuals who are asymptomatic for AIDS but are seropositive for HIV (dark histogram) have a lower expression of fluorescence intensity for CD44, CD54 and CD18 than do AIDS patients.

Turning to Table II, peripheral blood was collected and treated as above for FIG. 2; however, the collected cells also were treated with anti-CD8.

TABLE II

| Pt. Group | % Positive CD8 T Cells | | |
|---|---|---|---|
| | CD44 | CD18 | CD54 |
| Asymptomatic HIV+ | | | |
| 1 | 10 | 100 | 20 |
| 2 | 55 | 100 | 53 |
| 3 | 100 | 100 | 64 |
| 4 | 89 | 100 | 68 |
| 5 | 100 | 100 | 84 |
| AIDS | | | |

TABLE II-continued

| | % Positive CD8 T Cells | | |
|---|---|---|---|
| Pt. Group | CD44 | CD18 | CD54 |
| 1 | 100 | 100 | 32 |
| 2 | 100 | 100 | 39 |
| 3 | 100 | 100 | 71 |
| 4 | 100 | 100 | 40 |
| 5 | 100 | 100 | 76 |

As can be seen in the asymptomatic patients the number of CD44+/CD8+ and CD54+/CD8+ T cells is lower than in AIDS patients. This may relate to the function of these cells (or lack thereof) when the transition is reached.

All publications and patent applications mentioned in this specification are indicative of the level of ordinary skill in the art to which this invention pertains. All publications and patent applications are herein incorporated by reference to the same extent as if each individual publication or patent application was specifically and individually indicated to be incorporated by reference.

It will be apparent to one of ordinary skill in the art that many changes and modifications can be made in the invention without departing from the spirit or scope of the appended claims.

I claim:

1. A method for monitoring an HIV positive patient over time for conversion to AIDS comprising the steps of obtaining samples of whole blood over time from the patient, labelling cells in each sample of blood from the patient with a fluorescently labelled anti-CD44 monoclonal antibody and a fluorescently labelled anti-CD8 monoclonal antibody, measuring fluorescence intensity of CD44 on CD8+ cells in each sample by flow cytometry means and monitoring changes between samples over time in fluorescence intensity of CD44 on CD8+ cells.

2. The method of claim 1 wherein one of the fluorescent labels is phycoerythrin.

3. The method of claim 1 wherein one of the fluorescent labels is fluorescein isothiocyanate.

4. The method of claim 1 wherein the red cells in the whole blood are removed prior to measuring the fluorescence intensity.

5. The method of claim 4 wherein red cells are removed by lysis.

6. A method for monitoring an HIV positive patient over time for conversion to AIDS comprising the steps of obtaining samples of whole blood overtime from the patient, separating each sample into more than one aliquot, labelling cells in one aliquot from each sample of blood from the patient with a fluorescently labelled anti-CD8 monoclonal antibody and a fluorescently labelled anti-CD44 monoclonal antibody and in a second aliquot with a fluorescently labelled anti-CD8 monoclonal antibody and with a fluorescently labelled monoclonal second antibody selected from the group consisting of anti-CD18 and anti-CD54, measuring fluorescence intensity of CD44 and CD18 or CD54 on CD8+ cells in each aliquot respectively in each sample by flow cytometry means and monitoring changes between samples over time in fluorescence intensity of CD44 and CD18 or CD54 on CD8+ cells.

7. The method of claim 6 wherein one of the fluorescent labels is phycoerythrin.

8. The method of claim 6 wherein one of the fluorescent labels is fluorescein isothiocyanate.

9. The method of claim 6 wherein the red cells in the whole blood are removed prior to measuring the fluorescence intensity.

10. The method of claim 9 wherein red cells are removed by lysis.

11. The method of claim 6 wherein each sample is separated into three aliquots and anti-CD18 is added to one aliquot and anti-CD54 is added to the other aliquot.

* * * * *